(12) United States Patent
Li et al.

(10) Patent No.: US 8,729,222 B2
(45) Date of Patent: May 20, 2014

(54) ORGANIC THIN-FILM TRANSISTORS

(71) Applicant: Xerox Corporation, Norwalk, CT (US)

(72) Inventors: Yuning Li, Kitchener (CA); Yiliang Wu, Oakville (CA); Ping Liu, Mississauga (CA); Paul F. Smith, Oakville (CA)

(73) Assignee: Samsung Electronics Co. Ltd., Suwon-si (KR)

( * ) Notice: Subject to any disclaimer, the term of this patent is extended or adjusted under 35 U.S.C. 154(b) by 0 days.

(21) Appl. No.: 13/913,679

(22) Filed: Jun. 10, 2013

(65) Prior Publication Data

US 2013/0273688 A1 Oct. 17, 2013

Related U.S. Application Data

(62) Division of application No. 13/421,993, filed on Mar. 16, 2012, now Pat. No. 8,461,292, which is a division of application No. 12/273,585, filed on Nov. 19, 2008, now Pat. No. 8,154,013.

(51) Int. Cl.
C08G 75/00 (2006.01)

(52) U.S. Cl.
USPC .......................... 528/377; 528/380; 528/373

(58) Field of Classification Search
USPC .......................................... 528/377, 380, 373
See application file for complete search history.

(56) References Cited

U.S. PATENT DOCUMENTS

| 7,002,176 | B2 | 2/2006 | Iechi et al. |
| 7,172,823 | B2 | 2/2007 | Sohn et al. |
| 7,173,140 | B2 | 2/2007 | Li et al. |
| 7,276,728 | B2 | 10/2007 | Iechi et al. |
| 8,344,095 | B2 | 1/2013 | Miura et al. |
| 2004/0137271 | A1 | 7/2004 | Sohn et al. |
| 2006/0086933 | A1 | 4/2006 | Iechi et al. |
| 2006/0128969 | A1 | 6/2006 | Li et al. |
| 2007/0249087 | A1 | 10/2007 | Zhu et al. |
| 2009/0302743 | A1 | 12/2009 | Kato et al. |
| 2010/0117066 | A1 | 5/2010 | Heeney et al. |
| 2011/0213119 | A2 | 9/2011 | Miura et al. |

FOREIGN PATENT DOCUMENTS

| JP | 2004-128028 | 4/2004 |
| JP | 2004-146733 | 5/2004 |
| JP | 2004-204234 | 7/2004 |
| JP | 2006-183048 | 7/2006 |
| JP | 2007-019294 | 1/2007 |
| JP | 2007-088222 | 4/2007 |
| JP | 2008-004725 | 1/2008 |
| JP | 2008-147256 | 6/2008 |
| JP | 2009-190999 | 8/2009 |
| WO | 2007068618 | 6/2007 |

OTHER PUBLICATIONS

Hualong Pan et al., "Low-Temperature, Solution-Processed, High-Mobility Polymer Semiconductors for Thin-Film Transistor", Journal of American Chemical Society, American Chemical Society, Mar. 16, 2007, vol. 129, pp. 4112-4113.

Hualong Pan et al., Benzodithiophene Copolymer—A Low-Temperature, Solution-Processed High-Performance Semiconductor f, Advanced Functional Materials, Wiley-VCH, 2007, vol. 17, pp. 3574-3579.

Japanese Office Action dated Dec. 18, 2012 for Japanese Application No. 2009-258770 (with English translation).

Japanese Office Acton dated May 14, 2013 for Japanese Application No. 2009-258770 (with English translation).

*Primary Examiner* — Shane Fang

(74) *Attorney, Agent, or Firm* — Harness, Dickey & Pierce, P.L.C.

(57) ABSTRACT

A thin-film transistor comprises a semiconducting layer comprising a semiconducting material selected from Formula (I) or (II):

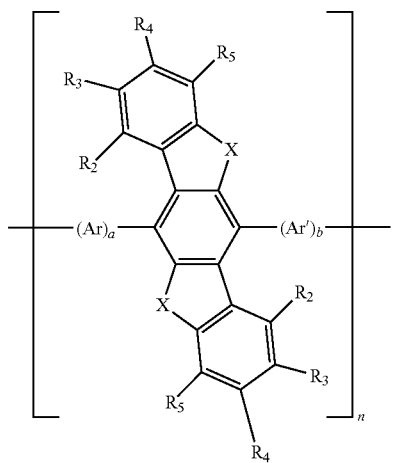
Formula (II)
wherein X, $R_1$, $R_2$, $R_3$, $R_4$, $R_5$ a, b, and n are as described herein. Semiconducting compositions of Formula (I) or (II) are also described.
20 Claims, 1 Drawing Sheet

ORGANIC THIN-FILM TRANSISTORS

CROSS-REFERENCE TO RELATED APPLICATIONS

This application is a divisional of U.S. patent application Ser. No. 13/421,993, filed Mar. 16, 2012, now U.S. Pat. No. 8,461,292, which is a divisional of U.S. patent application Ser. No. 12/273,585, filed Nov. 19, 2008, now U.S. Pat. No. 8,154,013. The disclosures of these applications are hereby fully incorporated by reference herein.

BACKGROUND

The present disclosure relates, in various embodiments, to compositions and processes suitable for use in electronic devices, such as thin film transistors ("TFT"s). The present disclosure also relates to components or layers produced using such compositions and processes, as well as electronic devices containing such materials.

Thin film transistors (TFTs) are fundamental components in modern-age electronics, including, for example, sensors, image scanners, and electronic display devices. TFT circuits using current mainstream silicon technology may be too costly for some applications, particularly for large-area electronic devices such as backplane switching circuits for displays (e.g., active matrix liquid crystal monitors or televisions) where high switching speeds are not essential. The high costs of silicon-based TFT circuits are primarily due to the use of capital-intensive silicon manufacturing facilities as well as complex high-temperature, high-vacuum photolithographic fabrication processes under strictly controlled environments. It is generally desired to make TFTs which have not only much lower manufacturing costs, but also appealing mechanical properties such as being physically compact, lightweight, and flexible. Organic thin film transistors (OTFTs) may be suited for those applications not needing high switching speeds or high densities.

TFTs are generally composed of a supporting substrate, three electrically conductive electrodes (gate, source and drain electrodes), a channel semiconducting layer, and an electrically insulating gate dielectric layer separating the gate electrode from the semiconducting layer.

It is desirable to improve the performance of known TFTs. Performance can be measured by at least three properties: the mobility, current on/off ratio, and threshold voltage. The mobility is measured in units of $cm^2/V \cdot sec$; higher mobility is desired. A higher current on/off ratio is desired. Threshold voltage relates to the bias voltage needed to be applied to the gate electrode in order to allow current to flow. Generally, a threshold voltage as close to zero (0) as possible is desired.

BRIEF DESCRIPTION

The present disclosure is directed, in various embodiments, to a thin film transistor having a semiconducting layer comprising a specific genus of semiconducting material. Semiconducting compositions are also disclosed.

Disclosed in some embodiments are thin-film transistors comprising a semiconducting layer. The semiconducting layer comprises a semiconducting material selected from Formula (I) or (II):

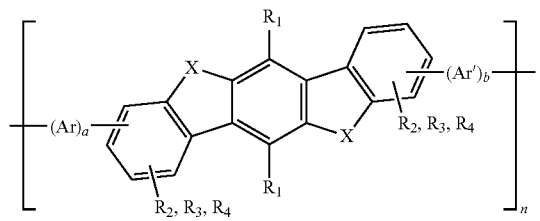

Formula (I)

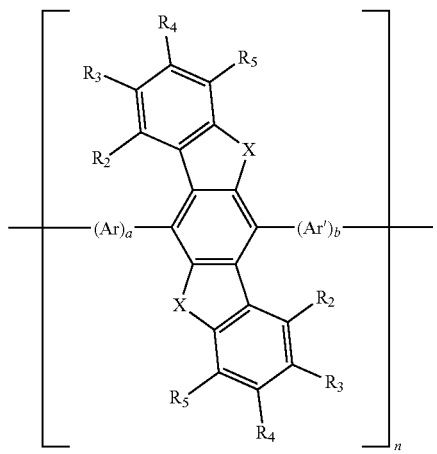

Formula (II)

wherein X is independently selected from S, Se, and O; $R_1$, $R_2$, $R_3$, $R_4$, and $R_5$ are independently selected from hydrogen, alkyl, substituted alkyl, aryl, substituted aryl, heteroaryl, halogen, —CN, and —NO$_2$; Ar and Ar' are independently a conjugated divalent moiety; a and b are integers of from 0 to about 10; and n is an integer and is at least 2.

In some embodiments, $R_2$, $R_3$, $R_4$, and $R_5$ are hydrogen. In other embodiments, at least one of $R_2$, $R_3$, $R_4$, and $R_5$ is alkyl. $R_1$ of Formula (I) may be an ethynylsilane.

Ar and Ar' may independently comprise a moiety selected from

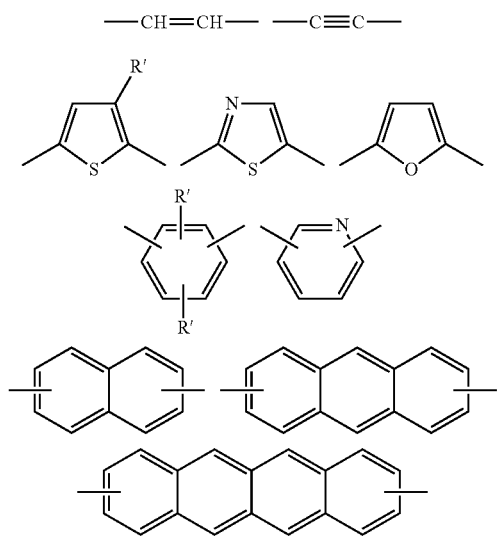

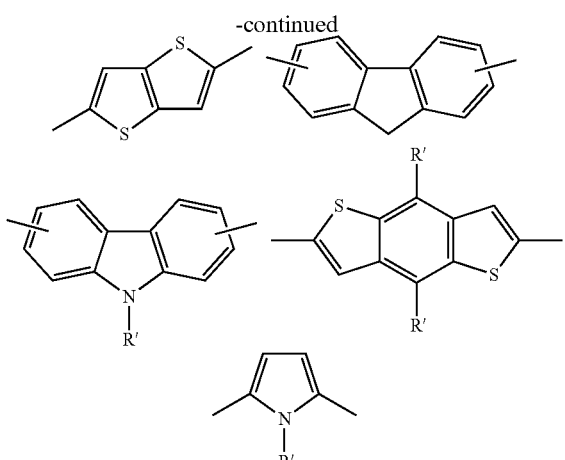

and combinations thereof, wherein R' is independently selected from hydrogen, alkyl, substituted alkyl, aryl, substituted aryl, heteroaryl, halogen, —CN, and —NO₂.

Ar and Ar' may both be:

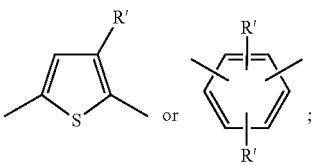

and a and b are each from 1 to about 5.

Each X may be sulfur. The semiconducting material may have a weight average molecular weight of from about 2,000 to about 200,000.

In other embodiments are disclosed semiconducting compositions comprising Formula (I) or (II).

In other specific embodiments, semiconducting compositions are disclosed which comprise a compound of Formula (I) or (II):

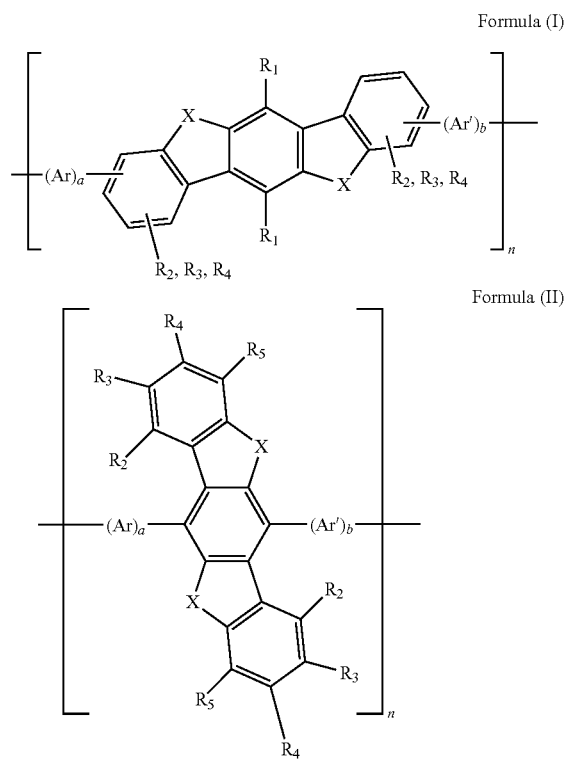

wherein X is sulfur;
R₁, R₂, R₃, R₄, and R₅ are independently selected from hydrogen, alkyl, substituted alkyl, aryl, substituted aryl, heteroaryl, halogen, —CN, and —NO₂;
Ar and Ar' are

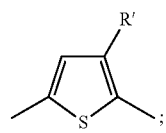

a and b are each an integer from 1 to about 5; and n is an integer and is at least 2.

Also included in further embodiments are the semiconducting layers and/or thin film transistors produced by this process.

These and other non-limiting characteristics of the exemplary embodiments of the present disclosure are more particularly described below.

BRIEF DESCRIPTION OF THE DRAWINGS

The following is a brief description of the drawings, which are presented for the purpose of illustrating the exemplary embodiments disclosed herein and not for the purpose of limiting the same.

DETAILED DESCRIPTION

Figure 1:
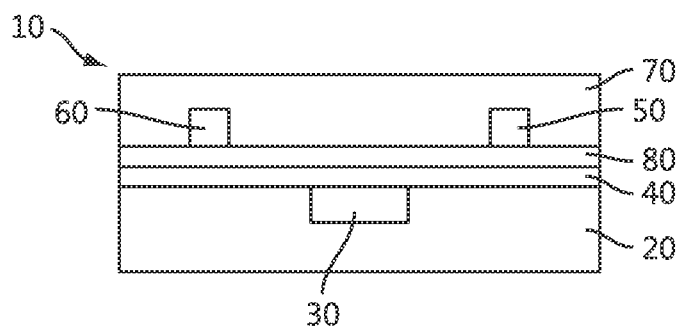
FIG. 1 is a first exemplary embodiment of a TFT of the present disclosure.

A more complete understanding of the components, processes, and apparatuses disclosed herein can be obtained by reference to the accompanying figures. These figures are merely schematic representations based on convenience and the ease of demonstrating the present development and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings and are not intended to define or limit the scope of the disclosure. In the drawings and the following description below, it is to be understood that like numeric designations refer to components of like function.

FIG. 1 illustrates a first OTFT embodiment or configuration. The OTFT 10 comprises a substrate 20 in contact with the gate electrode 30 and a dielectric layer 40. Although here the gate electrode 30 is depicted within the substrate 20, this is not required. However, of some importance is that the dielectric layer 40 separates the gate electrode 30 from the source electrode 50, drain electrode 60, and the semiconducting layer 70. The source electrode 50 contacts the semiconducting layer 70. The drain electrode 60 also contacts the semiconducting layer 70. The semiconducting layer 70 runs over and between the source and drain electrodes 50 and 60. Optional interfacial layer 80 is located between dielectric layer 40 and semiconducting layer 70.

Figure 2:
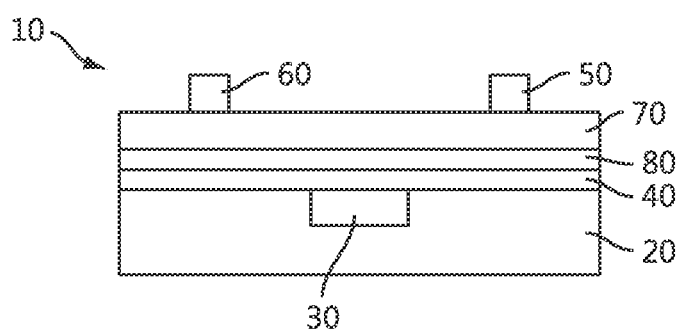
FIG. 2 is a second exemplary embodiment of a TFT of the present disclosure.

FIG. 2 illustrates a second OTFT embodiment or configuration. The OTFT 10 comprises a substrate 20 in contact with the gate electrode 30 and a dielectric layer 40. The semiconducting layer 70 is placed over or on top of the dielectric layer 40 and separates it from the source and drain electrodes 50 and 60. Optional interfacial layer 80 is located between dielectric layer 40 and semiconducting layer 70.

Figure 3:
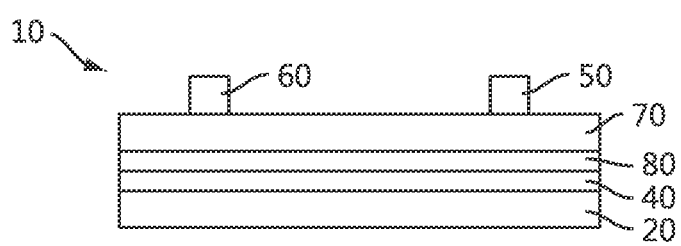
FIG. 3 is a third exemplary embodiment of a TFT of the present disclosure.

FIG. 3 illustrates a third OTFT embodiment or configuration. The OTFT 10 comprises a substrate 20 which also acts as the gate electrode and is in contact with a dielectric layer 40. The semiconducting layer 70 is placed over or on top of the dielectric layer 40 and separates it from the source and drain electrodes 50 and 60. Optional interfacial layer 80 is located between dielectric layer 40 and semiconducting layer 70.

Figure 4:
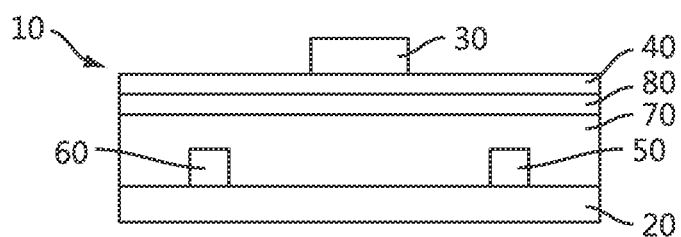
FIG. 4 is a fourth exemplary embodiment of a TFT of the present disclosure.

FIG. 4 illustrates a fourth OTFT embodiment or configuration. The OTFT 10 comprises a substrate 20 in contact with the source electrode 50, drain electrode 60, and the semiconducting layer 70. The semiconducting layer 70 runs over and between the source and drain electrodes 50 and 60. The dielectric layer 40 is on top of the semiconducting layer 70. The gate electrode 30 is on top of the dielectric layer 40 and does not contact the semiconducting layer 70. Optional interfacial layer 80 is located between dielectric layer 40 and semiconducting layer 70.

The present disclosure relates to a thin-film transistor comprising a semiconducting layer or a semiconducting composition. The semiconducting layer or semiconducting composition comprises a semiconducting material selected from Formula (I) or (II):

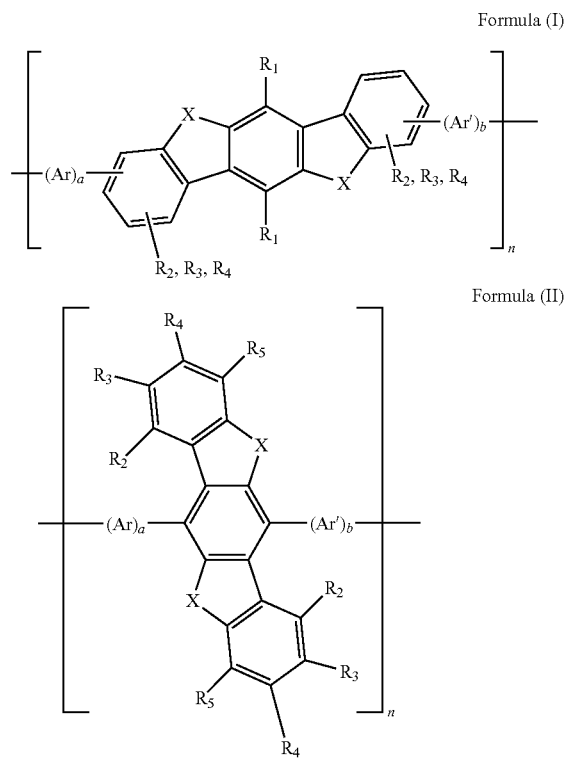

Formula (I)

Formula (II)

wherein X is independently selected from S, Se, and O; $R_1$, $R_2$, $R_3$, $R_4$, and $R_5$ are independently selected from hydrogen, alkyl, substituted alkyl, aryl, substituted aryl, heteroaryl, halogen, —CN, and —NO$_2$; Ar and Ar' are independently a conjugated divalent moiety; a and b are integers of from 0 to about 10; and n is an integer and is at least 2.

Again, the alkyl group generally contains 1 to about 20 carbon atoms and the aryl group contains from about 6 to about 20 carbon atoms. Although a and b may each be zero, generally in embodiments a and b are each at least one. In some embodiments, (a+b)>0. In some embodiments, $R_1$, $R_2$, $R_3$, $R_4$, and $R_5$ are independently selected from hydrogen and $C_1$-$C_{20}$ alkyl. In other embodiments, $R_2$, $R_3$, $R_4$, and $R_5$ are hydrogen. In other embodiments, at least one of $R_2$, $R_3$, $R_4$, and $R_5$ is alkyl.

When an alkyl or aryl group is substituted, it may be substituted with a silyl, alkyl, alkoxy, aryl, halogen, or heteroaryl group, or combinations thereof. Exemplary heteroaryl groups include thienyl, furanyl, pyridinyl, oxazoyl, pyrroyl, triazinyl, imidazoyl, pyrimidinyl, pyrazinyl, oxadiazoyl, pyrazoyl, triazoyl, thiazoyl, thiadiazoyl, quinolinyl, quinazolinyl, naphthyridinyl, and carbazoyl.

In embodiments, $R_1$ is an ethynylsilane. The ethynylsilane may be substituted with three alkyl groups.

Ar and Ar' may independently comprise a moiety selected from

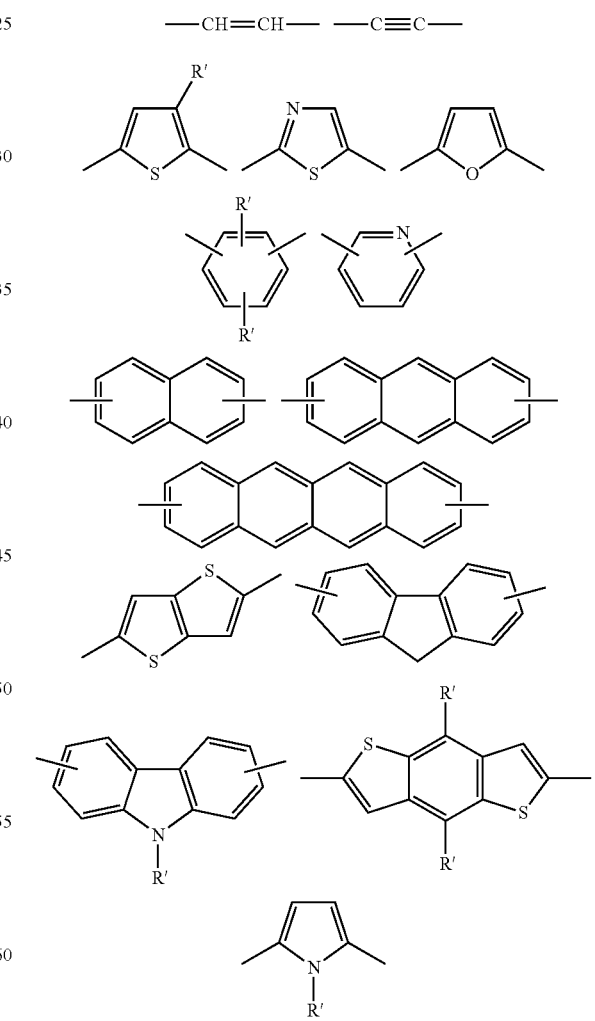

and combinations thereof, wherein R' is independently selected from hydrogen, alkyl, substituted alkyl, aryl, substituted aryl, heteroaryl, halogen, —CN, and —NO$_2$.

In some embodiments, Ar and Ar' are both

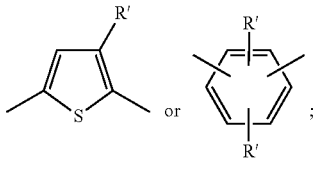

and a and b are each from 1 to about 5.

In other embodiments, each X is sulfur. The semiconducting material may have a weight average molecular weight of from about 2,000 to about 200,000, including from about 5,000 to about 100,000.

Polymers of Formulae (I) and (II) can be prepared using any appropriate methods. For example, polymers of Formula (I) can be prepared using Suzuki coupling polymerization of dihalogen compound 1 with diboronic acid 2 as shown in Scheme 1. For the synthesis of polymers of Formula (II), the dibromo monomer 4 can be readily prepared through bromination of compound 3 using for instance N-bromosuccinimide (NBS), and then the dibromo compound 4 can be polymerized into polymer (II) via zinc-mediated dehalogenative coupling reaction in the presence of a nickel-based catalyst such as $NiCl_2/,2,2'$-bipyridine.

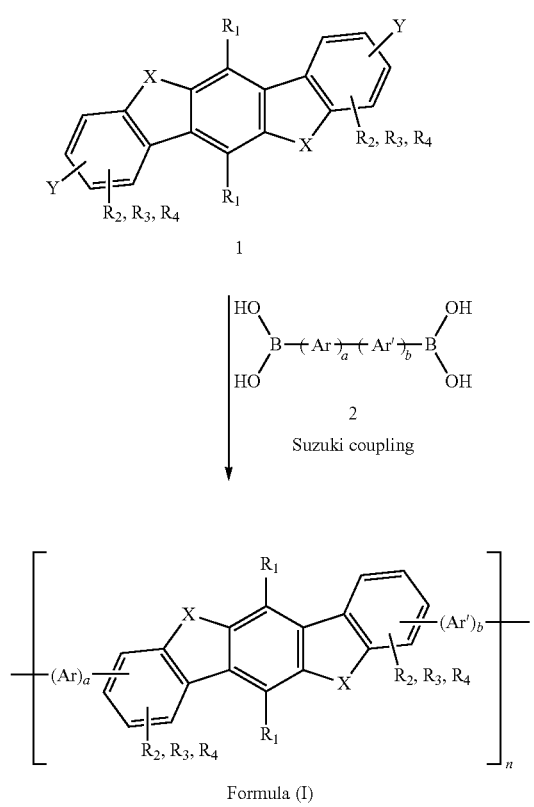

Scheme 1. Exemplary synthesis of Formula (I) via Suzuki coupling polymerization.

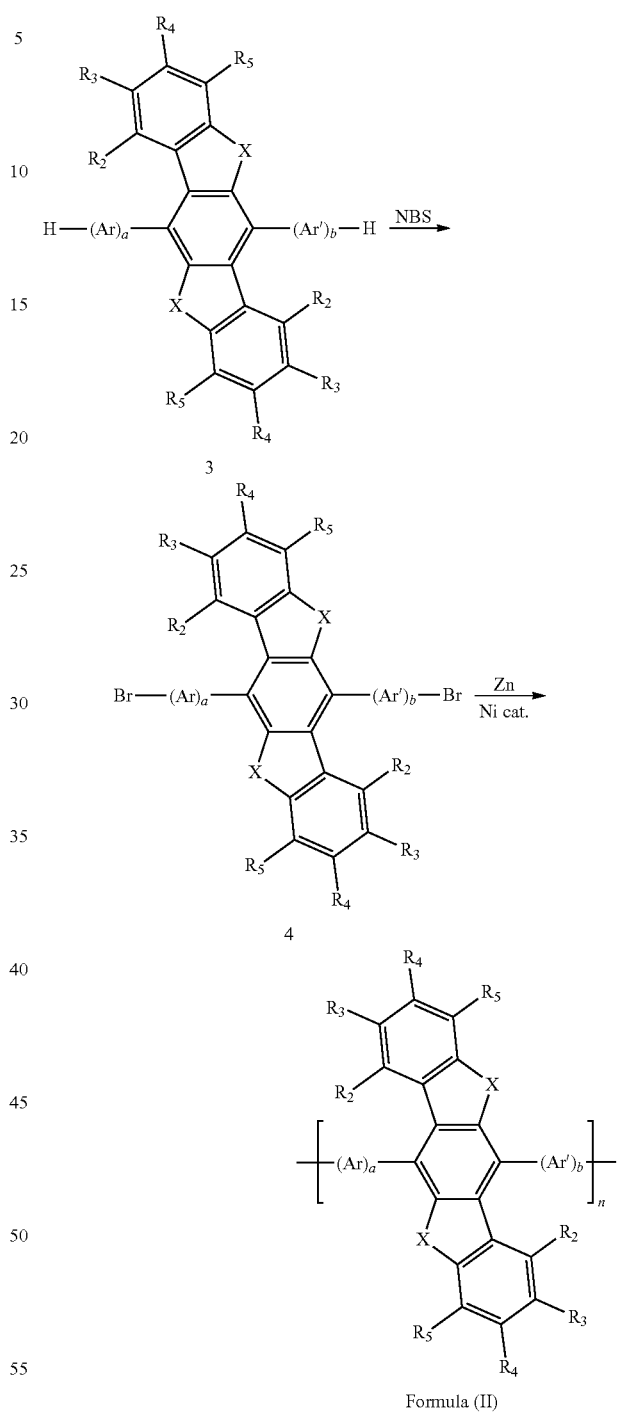

Scheme 2. Exemplary synthesis of Formula (II) via dehalogenative coupling polymerization using zinc.

If desired, the semiconducting layer may further comprise another organic semiconductor material. Examples of other organic semiconductor materials include but are not limited to acenes, such as anthracene, tetracene, pentacene, and their substituted derivatives, perylenes, fullerenes, oligothiophenes, other semiconducting polymers such as triarylamine polymers, polyindolocarbazole, polycarbazole, polyacenes, polyfluorene, polythiophenes and their substituted derivatives, phthalocyanines such as copper phthalocyanines or zinc phthalocyanines and their substituted derivatives.

The semiconducting layer is from about 5 nm to about 1000 nm thick, especially from about 10 nm to about 100 nm thick. The semiconducting layer can be formed by any suitable method. However, the semiconducting layer is generally formed from a liquid composition, such as a dispersion or solution, and then deposited onto the substrate of the transistor. Exemplary deposition methods include liquid deposition such as spin coating, dip coating, blade coating, rod coating, screen printing, stamping, ink jet printing, and the like, and other conventional processes known in the art.

The substrate may be composed of materials including but not limited to silicon, glass plate, plastic film or sheet. For structurally flexible devices, plastic substrate, such as for example polyester, polycarbonate, polyimide sheets and the like may be used. The thickness of the substrate may be from about 10 micrometers to over 10 millimeters with an exemplary thickness being from about 50 micrometers to about 5 millimeters, especially for a flexible plastic substrate and from about 0.5 to about 10 millimeters for a rigid substrate such as glass or silicon.

The gate electrode is composed of an electrically conductive material. It can be a thin metal film, a conducting polymer film, a conducting film made from conducting ink or paste or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite or silver colloids. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges from about 10 to about 500 nanometers for metal films and from about 0.5 to about 10 micrometers for conductive polymers.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

If desired, an interfacial layer may be placed between the dielectric layer and the semiconducting layer. As charge transport in an organic thin film transistor occurs at the interface of these two layers, the interfacial layer may influence the TFT's properties. Exemplary interfacial layers may be formed from silanes, such as those described in U.S. patent application Ser. No. 12/101,942, filed Apr. 11, 2008.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order, as is seen in the Figures. The term "upon the substrate" should not be construed as requiring that each component directly contact the substrate. The term should be construed as describing the location of a component relative to the substrate. Generally, however, the gate electrode and the semiconducting layer should both be in contact with the dielectric layer. In addition, the source and drain electrodes should both be in contact with the semiconducting layer. The semiconducting polymer formed by the methods of the present disclosure may be deposited onto any appropriate component of an organic thin-film transistor to form a semiconducting layer of that transistor.

The resulting transistor may have, in embodiments, a mobility of 0.01 cm$^2$/V·sec or greater, including 0.1 cm$^2$/V·sec or greater, and/or a current on/off ratio of $10^4$ or more.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for forming a semiconductor layer, comprising:
    depositing a liquid composition onto a substrate to form the semiconducting layer;
    wherein the liquid composition comprises a semiconducting material selected from Formula (I) or Formula (II):

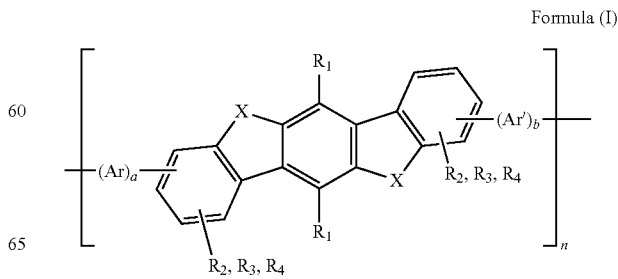

Formula (I)

-continued

Formula (II)

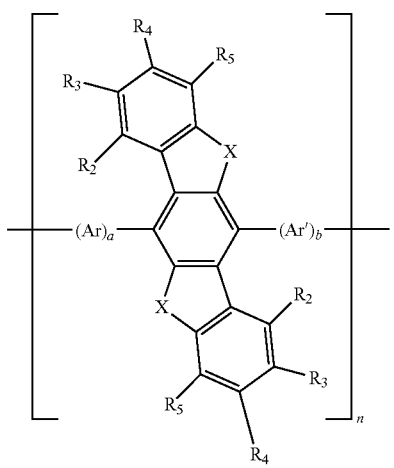

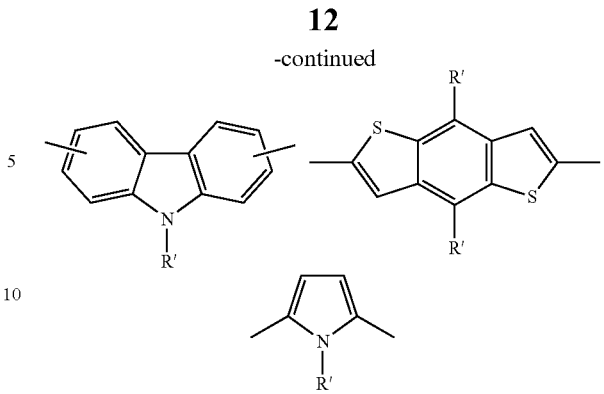

and combinations thereof, wherein R' is independently selected from hydrogen, alkyl, substituted alkyl, aryl, substituted aryl, heteroaryl, halogen, —CN, and —NO₂.

6. The method of claim 5, wherein Ar anti Ar' are both

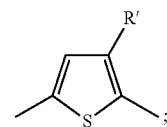

and
wherein a and b are each from 1 to about 5.

7. The semiconducting material of claim 5, wherein Ar and Ar' are both

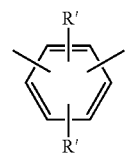

wherein a and b are each from 1 to about 5.

wherein X is independently selected from S and Se in Formula (I) and X is independently selected from S, Se, and O in Formula (II);
R₁ is independently selected from hydrogen, alkyl, substituted alkyl, aryl, substituted aryl, heteroaryl, halogen, —CN, —NO₂, and ethynylsilane;
R₂, R₃, R₄, and R₅ are independently selected from hydrogen, alkyl, substituted alkyl, aryl, substituted aryl, heteroaryl, halogen, —CN, and —NO₂;
Ar and Ar' are independently a conjugated divalent moiety;
a and b are independently integers from 1 to about 10; and
n is an integer and is at least 2.

2. The method of claim 1, wherein R₂, R₃, R₄, and R₅ are hydrogen.

3. The method of claim 1, wherein at least one of R₂, R₃, R₄, and R₅ is alkyl.

4. The method of claim 1, wherein the ethynylsilane is substituted with three alkyl groups.

5. The method of claim 1, wherein Ar and Ar' independently comprise a moiety selected from

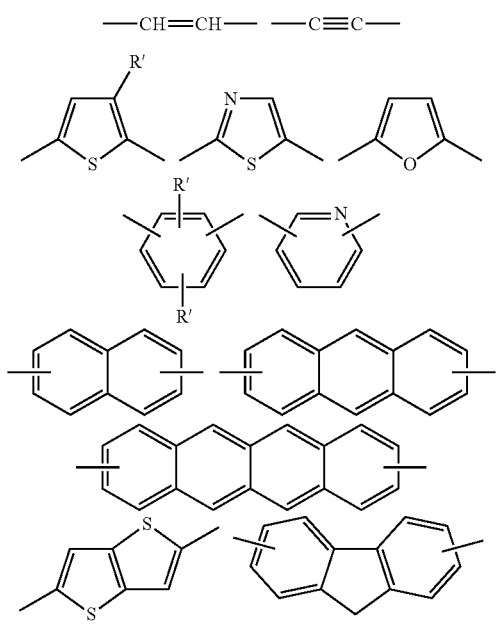

8. The method of claim 1, wherein each X is sulfur.

9. The method of claim 1, wherein the semiconducting material has a weight average molecular weight of from about 2,000 to about 200,000.

10. The method of claim 1, wherein a and b are independently integers from 1 to about 5.

11. The method of claim 1, wherein the depositing comprises spin coating, dip coating, blade coating, rod coating, screen printing, stamping, or ink jet printing.

12. The method of claim 1, wherein the semiconducting layer has a thickness of from about 5 nm to about 1000 nm.

13. The method of claim 1, wherein the semiconducting layer has a thickness of from about 10 nm to about 100 nm.

14. The method of claim 1, wherein the substrate is composed of silicon, glass plate, plastic film, or plastic sheet.

15. The method of claim 1, wherein the substrate has a thickness of from about 10 micrometers to about 10 millimeters.

16. The method of claim 1, wherein the substrate has a thickness of from about 50 micrometers to about 5 millimeters.

17. The method of claim 1, wherein the substrate has a thickness of from about 0.5 to about 10 millimeters.

18. The method of claim 1, wherein the semiconducting material is of Formula (I).

19. The method of claim 1, wherein the semiconducting material is of Formula (II).

20. The method of claim 1, wherein the semiconducting layer further comprises another semiconducting material selected from the group consisting of an acene a perylene, a fullerene, an oligothiophene, a triarylamine polymer, a polyindolocarbazole, a polycarbazole, a polyacene, a polyfluorene, a polythiophene, and a phthalocyanine.

\* \* \* \* \*

UNITED STATES PATENT AND TRADEMARK OFFICE
CERTIFICATE OF CORRECTION

| | | |
|---|---|---|
| PATENT NO. | : 8,729,222 B2 | Page 1 of 1 |
| APPLICATION NO. | : 13/913679 | |
| DATED | : May 20, 2014 | |
| INVENTOR(S) | : Li et al. | |

It is certified that error appears in the above-identified patent and that said Letters Patent is hereby corrected as shown below:

Title Page, should read,

(71)     Applicant:   SAMSUNG ELECTRONICS CO., LTD., Gyeonggi-do (KR)

(72)     Inventors:   Yuning Li, Singapore (SG); Yiliang Wu, Oakville (CA); Ping Liu, Mississauga (CA); Paul F. Smith, Oakville (CA)

Signed and Sealed this
Eighteenth Day of August, 2015

Michelle K. Lee
*Director of the United States Patent and Trademark Office*